United States Patent
Straka

(10) Patent No.: US 10,603,799 B2
(45) Date of Patent: Mar. 31, 2020

(54) SYSTEM FOR USE WITH ENCODED END EFFECTORS AND RELATED METHODS OF USE

(71) Applicant: L'Oreal, Paris (FR)

(72) Inventor: Scott Straka, Redmond, WA (US)

(73) Assignee: L'Oreal, Paris (FR)

( * ) Notice: Subject to any disclaimer, the term of this patent is extended or adjusted under 35 U.S.C. 154(b) by 257 days.

(21) Appl. No.: 15/639,544

(22) Filed: Jun. 30, 2017

(65) Prior Publication Data

US 2019/0001503 A1   Jan. 3, 2019

(51) Int. Cl.
| | | |
|---|---|---|
| A61B 17/00 | (2006.01) | |
| B25J 13/08 | (2006.01) | |
| A46B 15/00 | (2006.01) | |
| A46B 13/02 | (2006.01) | |
| A61C 17/22 | (2006.01) | |
| A46B 13/00 | (2006.01) | |

(52) U.S. Cl.
CPC ........... B25J 13/087 (2013.01); A46B 13/02 (2013.01); A46B 15/0004 (2013.01); A61C 17/221 (2013.01); *A46B 13/008* (2013.01); *A46B 2200/102* (2013.01)

(58) Field of Classification Search
CPC .... A61B 2017/00477; A61B 2034/305; A61B 34/30; B25J 3/00; B25J 13/087; Y10S 901/10; Y10S 901/29; A46B 15/0004; A46B 2200/102

USPC ................ 700/245, 247, 250, 253; 606/130; 901/10, 15, 29; 318/568.11, 568.16
See application file for complete search history.

(56) References Cited

U.S. PATENT DOCUMENTS

| | | | |
|---|---|---|---|
| 4,900,252 A | 2/1990 | Liefke et al. | |
| 5,749,885 A | 5/1998 | Sjostrom et al. | |
| 6,899,538 B2 | 5/2005 | Matoba | |
| 8,035,487 B2 | 10/2011 | Malackowski | |
| 8,443,475 B2 | 5/2013 | Hilscher | |
| 2005/0000044 A1 | 1/2005 | Hilscher et al. | |
| 2008/0209650 A1* | 9/2008 | Brewer ............. | A46B 15/0002 15/22.1 |
| 2013/0206814 A1* | 8/2013 | Morgan .......... | A61B 17/07207 227/176.1 |
| 2015/0305969 A1 | 10/2015 | Giraud et al. | |
| 2017/0049278 A1 | 2/2017 | Thomassen | |
| 2017/0095070 A1 | 4/2017 | Machiorlette et al. | |

FOREIGN PATENT DOCUMENTS

| | | |
|---|---|---|
| DE | 10 2013 202 580 A1 | 8/2014 |
| WO | 2017017541 A1 | 2/2017 |

OTHER PUBLICATIONS

International Search Report and Written Opinion dated Oct. 1, 2018 in corresponding Application No. PCT/US2018/038211, filed Jun. 19, 2018, 13 pgs.

* cited by examiner

*Primary Examiner* — Dalena Tran
(74) *Attorney, Agent, or Firm* — Christensen O'Connor Johnson Kindness PLLC

(57) ABSTRACT

Systems configured to couple with and identify encoded end effectors and related methods of use are described.

20 Claims, 5 Drawing Sheets

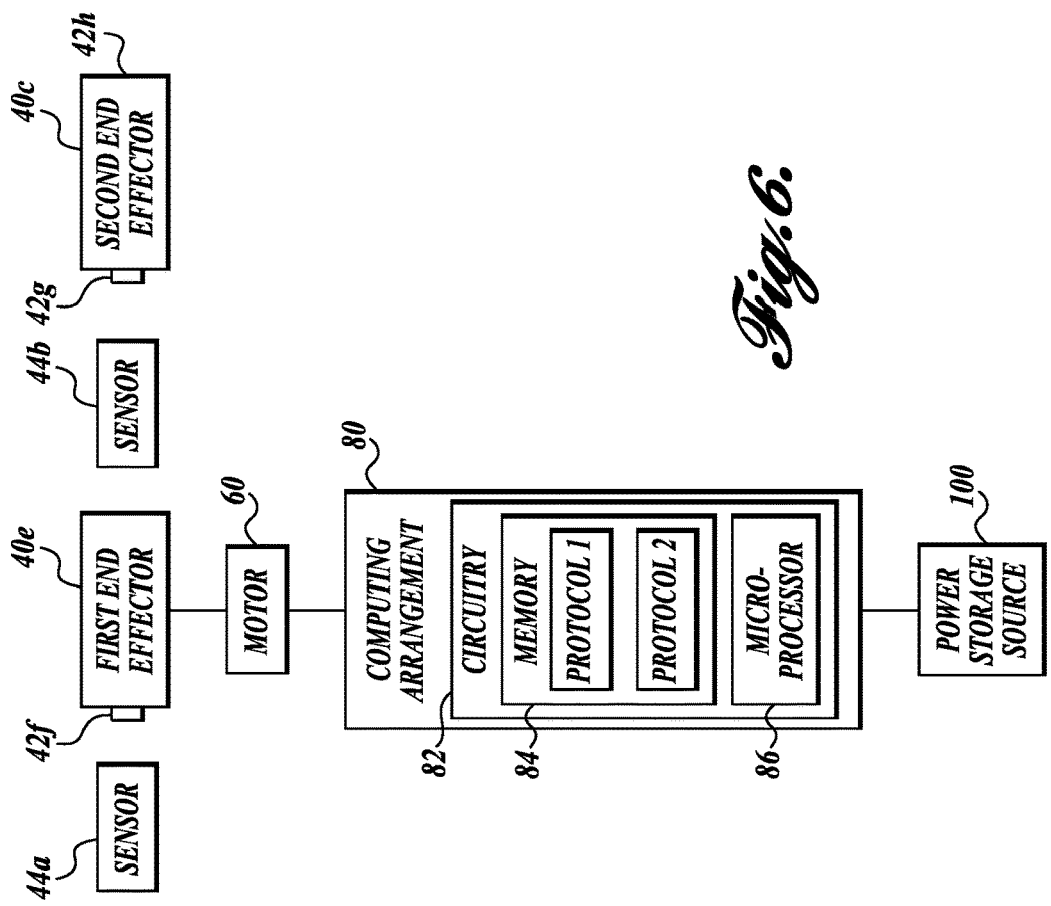
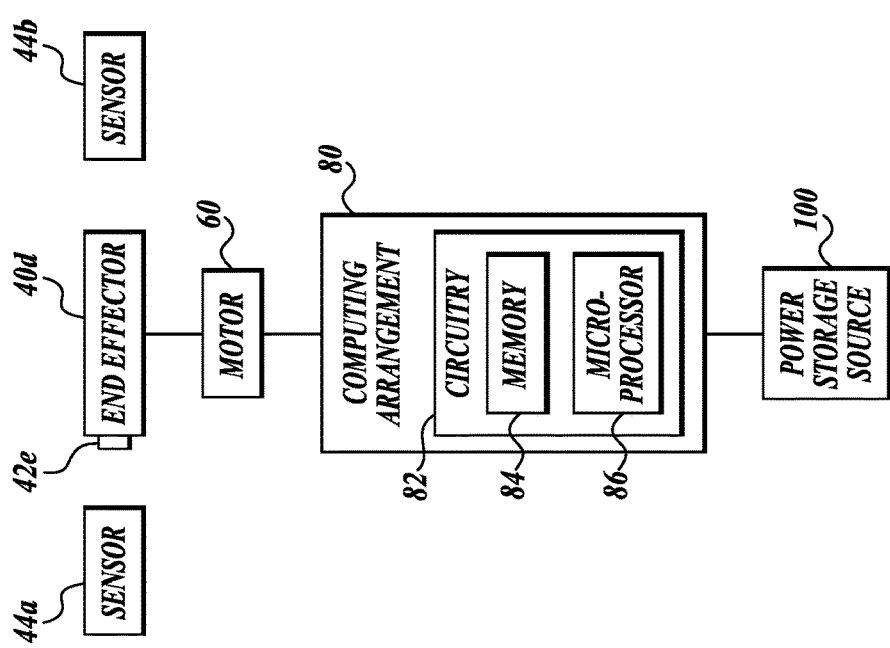

SYSTEM FOR USE WITH ENCODED END EFFECTORS AND RELATED METHODS OF USE

SUMMARY

Examples of the present disclosure seek to address the problems associated with identifying an end effector coupled to a system or appliance, such as a handheld personal care appliance, and operating according to protocols or parameters corresponding to the identified end effector. In this regard, examples described herein relate to systems and appliances that include a sensor configured to detect a presence or absence of a detectable element associated with a detachable end effector operably coupleable to a motor and a computing arrangement including circuitry configured to actuate the motor and to determine an inertia of the end effector. Such systems are configured to identify an end effector coupled to the system and operate in a manner and according to parameters corresponding to the identified end effector coupled to the system.

In an aspect, the present disclosure provides a system generally including a first sensor configured to detect a presence or absence of a detectable element associated with a detachable end effector operably coupled to a motor; and a computing arrangement including circuitry configured to actuate the motor and to determine an inertia of the end effector.

In another aspect, the present disclosure provides an appliance generally including an end effector operably coupled to a motor, the end effector including a number of detectable elements greater than or equal to zero; a plurality of sensors configured to detect the presence or absence of the number of detectable elements; and a computing arrangement including circuitry configured to actuate the motor and to determine an inertia of the end effector; wherein the computing arrangement is configured to identify the end effector based on a measurand associated with the number detectable elements and the inertia of the end effector.

In accordance with any of the embodiments disclosed herein, a sensor is configured to detect an attribute associated with the detectable element chosen from at least one of a location, a polarity, a magnetic susceptibility, a magnitude of a magnetic field, a geometric arrangement, a magnetic field distribution, and a capacitance.

In accordance with any of the embodiments disclosed herein, a sensor is configured to detect an attribute associated with two or more detectable elements chosen from a geometric configuration, a location, a polarity, a magnetic susceptibility, a magnitude of a magnetic field, a geometric arrangement, a magnetic field distribution, and a capacitance.

In accordance with any of the embodiments disclosed herein, the computing arrangement includes circuitry configured to actuate the motor and to determine the inertia of the end effector based on one or more signal parameters associated with actuation of the motor chosen from a signal amplitude, a signal frequency, and a signal waveform shape.

In accordance with any of the embodiments disclosed herein, the computing arrangement includes circuitry configured to modulate one or more of an operating frequency, an operating duration, an operating intensity, a haptic protocol, a treatment protocol, and a duty cycle responsive to one or more inputs indicative of a detected element and a determined inertia of the end effector. In accordance with any of the embodiments disclosed herein, the one or more inputs indicative of a detected element are an attribute associated with the detectable element.

In accordance with any of the embodiments disclosed herein, a detectable element includes at least one magnet.

In accordance with any of the embodiments disclosed herein, a sensor is chosen from a Hall effect sensor, a capacitance sensor, an inductance sensor, and a magnetic susceptibility.

In accordance with any of the embodiments disclosed herein, the system or appliance includes a second sensor associated with the system, wherein the second sensor is configured to detect a presence or absence of a detectable element associated with the end effector. In accordance with any of the embodiments disclosed herein, the second sensor is configured to detect an attribute associated with the detectable element chosen from a location, a polarity, a magnetic susceptibility, a magnitude of the magnetic field, and a capacitance. In accordance with any of the embodiments disclosed herein, the number of sensors is greater than the number of detectable elements.

In accordance with any of the embodiments disclosed herein, the computing arrangement is configured to identify the end effector based on the presence or absence of the detectable element and the inertia of the end effector.

In accordance with any of the embodiments disclosed herein, the computing arrangement including circuitry configured to actuate the motor and to determine an inertia of the end effector is configured to determine a rotational inertia of the end effector, and wherein the computing arrangement is configured to: actuate the motor with a known force to oscillate the end effector about a starting position; count the number of times the end effector passes the starting position in a given time; and calculate the rotational inertia of the end effector.

In accordance with any of the embodiments disclosed herein, the computing arrangement including circuitry configured to actuate the motor and to determine an inertia of the end effector is configured to determine a rotational inertia of the end effector, and wherein the computing arrangement is configured to: actuate the motor with a known force to oscillate the end effector about a starting position; measure a maximum amplitude of the end effector oscillation after a given time; and calculate the rotational inertia of the end effector.

In accordance with any of the embodiments disclosed herein, the end effector is a first end effector, wherein the motor is configured to operably couple to a second end effector when the first end effector is not in use, and wherein the computing arrangement includes circuitry configured to modulate one or more of an operating frequency, an operating duration, an operating intensity, a haptic protocol, a treatment protocol, and a duty cycle responsive to one or more inputs indicative of a detected element and a determined inertia of the second end effector. In accordance with any of the embodiments disclosed herein, the second end effector includes a second detectable element different from the detectable element of the first end effector; and wherein the first sensor is configured to detect signals indicative of the presence or absence of the second detectable element.

In accordance with any of the embodiments disclosed herein, the second end effector has an inertia different from the first end effector.

In another aspect, the present disclosure provides a method of identifying an end effector coupled to a motor of system comprising: generating inertia information associated with the end effector; and determining the identity of the end effector based on the presence or absence of a number of detectable elements associated with the end effector and at least one input indicative of the inertia of the end effector.

In accordance with any of the embodiments disclosed herein, generating inertia information associated with the end effector includes generating rotational inertia information; and wherein the rotational inertia information is generated by: actuating the motor with a known force to oscillate the end effector about a starting position; counting the number of times the end effector passes the starting position in a given time; and calculating the rotational inertia of the end effector.

In accordance with any of the embodiments disclosed herein, generating inertia information associated with the end effector includes generating rotational inertia information; and wherein the rotational inertia information is generated by: actuating the motor with a known force to oscillate the end effector about a starting position; measuring a maximum amplitude of the end effector oscillation decay after a given time; and calculating the rotational inertia of the end effector.

This summary above is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

FIG. 5 schematically illustrates a system in accordance with an aspect of the disclosure coupled to an end effector; and FIG. 6 schematically illustrates the system of FIG. 5, an end effector coupled to the system, and a second end effector coupleable to the system.

DETAILED DESCRIPTION

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

The present disclosure relates generally to handheld personal care appliances, systems, and methods. Generally described, personal care appliances typically use end effectors to produce a desired effect on a portion of a body of a user. Examples of such appliances include power skin brushes, power toothbrushes, and shavers, among others.

A given personal care appliance may operably couple with a variety of end effectors and include a variety of treatment protocols corresponding to the particular end effectors. If the appliance operates a motor according to a protocol intended for an end effector with a larger or smaller inertia, for example, than the one coupled to the motor the predetermined operation parameters may not be executed properly. Additionally, end effectors having the same or similar inertias may have different, for example, end effectors surfaces and intended uses. Further, after extended use an end effector may be worn or dirty, requiring replacement. It would be useful to provide to a user an indication that an end effector should be replaced.

Toward that end, the following discussion provides examples of systems that include a first sensor configured to detect a presence or absence of a detectable element associated with a detachable end effector operably coupleable to a motor. As will be described in more detail below, the system further includes a computing arrangement including circuitry configured to actuate the motor and to determine an inertia of the end effector. In that regard, as will be described in more detail below, the computing arrangement is configured to identify the end effector operably coupled to the motor and to operate the motor according to one or more protocols corresponding to the end effector.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Figure 1:
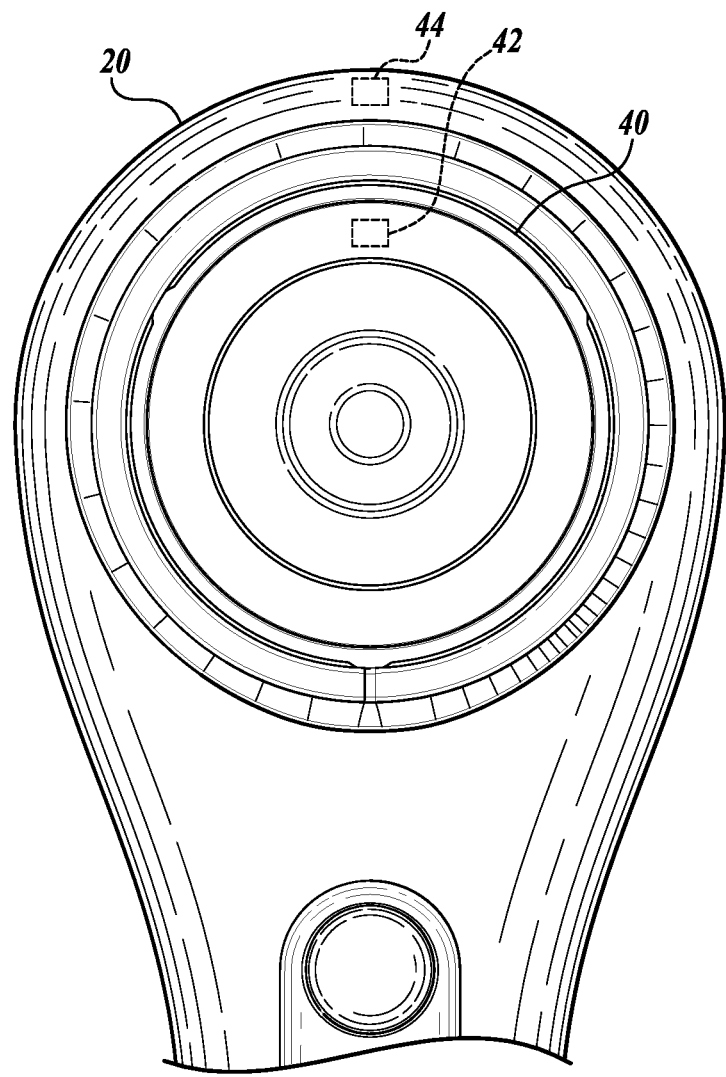
FIG. 1 is a side view of a system in accordance with an aspect of the disclosure coupled to an end effector.

FIG. 1 illustrates a representative system 20 coupled to an end effector 40, together a personal care appliance. As shown, the end effector 40 includes a detectable element 42 associated with the effector 40. The system 20 further includes a sensor 44 configured to detect a presence or absence of the detectable element 42. In this regard, the sensor is configured to detect an attribute associated with the detectable element 42. In an embodiment, the attribute associated with the detectable element 42 is chosen from a location, a geometric arrangement, a magnetic field distribution, a polarity, a magnetic susceptibility, a magnitude of a magnetic field, a capacitance of the detectable element 42, and the like. In an embodiment, the attribute associated with the detectable element 42 is a difference between a reference condition and at least one of a location, a geometric arrangement, a magnetic field distribution, a polarity, a magnetic susceptibility, a magnitude of a magnetic field, a capacitance of the detectable element 42, and the like. As will be described in more detail below, by detecting the presence or absence of detectable elements in conjunction with inertia information associated with the end effector 40, the system 20 is configured to identify the end effector 40.

As will be described further herein, in an embodiment, the end effector 40 includes two or more detectable elements 42 associated with the end effector 40. In an embodiment, the end effector 40 includes 3, 4, 5, 6, 7, 8, 9, 10, or more detectable elements associated with the end effector 40. In an embodiment, the end effector 40 includes no detectable elements 42 associated with the end effector 40. In an embodiment, the two or more detectable elements 42 are distributed radially equidistant about the end effector 40.

In an embodiment, one or each detectable element 42 is a magnet. In another embodiment, one or each detectable element 42 includes a capacitive element.

In an embodiment, the sensor 44 is a Hall effect sensor. In an embodiment, the sensor 44 is a capacitive sensor and one or each detectable element 42 includes a capacitive element. In an embodiment, the sensor 44 is an inductance sensor. In an embodiment, the sensor 44 is a magnetic susceptibility sensor.

In an embodiment, the sensor 44 is configured to detect an attribute associated with two or more detectable elements 42 associated with the end effector 40. In an embodiment, the sensor 44 is configured to detect a difference in an attribute associated with two or more detectable elements 42 associated with the end effector 40. In an embodiment, the attribute associated with two or more detectable elements 42 is chosen from a geometric configuration, a location, a polarity, a magnetic susceptibility, a magnitude of a magnetic field, and a capacitance.

Figure 2:
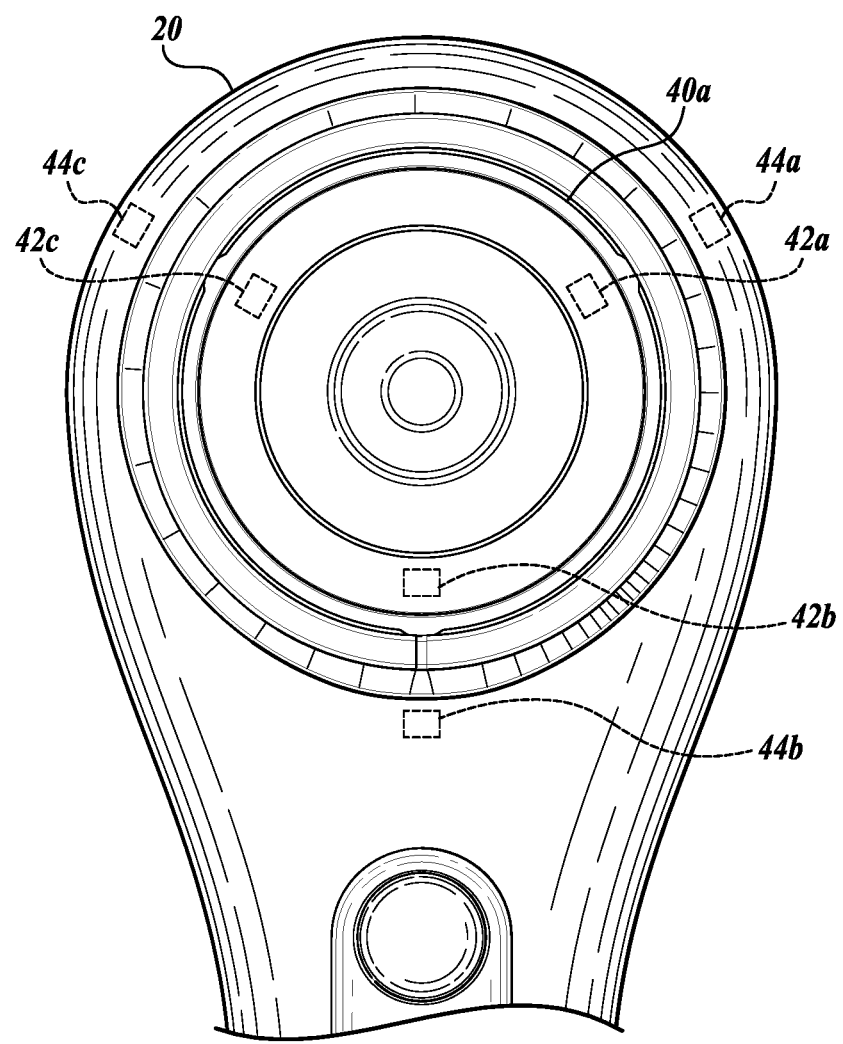
FIG. 2 is a side view of another system in accordance with an aspect of the disclosure coupled to an end effector.

In an embodiment, the system includes two or more sensors. In that regard, attention is directed to FIG. 2, where representative embodiments of a system 20 and an end effector 40a are illustrated. As shown, system 20 includes sensors 44a, 44b, and 44c configured to detect an attribute associated with detectable elements 42a, 42b, and 42c associated with the end effector 40a. The plurality of sensors 44a, 44b, and 44c and corresponding detectable elements 42a, 42b, and 42c allow for additional degrees of encoding of the end effector 40a over an end effector including a single detectable element and a single sensor. In this regard, the system 20 is configured to detect an attribute associated with two or more of the detectable elements 42a, 42b, and 42c. Further, in this regard, the system 20 is configured to identify a number of end effectors 40 based, in part, upon detecting attributes associated with the two or more detectable elements 42a, 42b, and 42c. Additionally, in this regard, the system 20 is configured to distinguish between end effectors 40 having the same or a similar inertia, but with, for example, different end effector surfaces or intended function.

Figure 3:
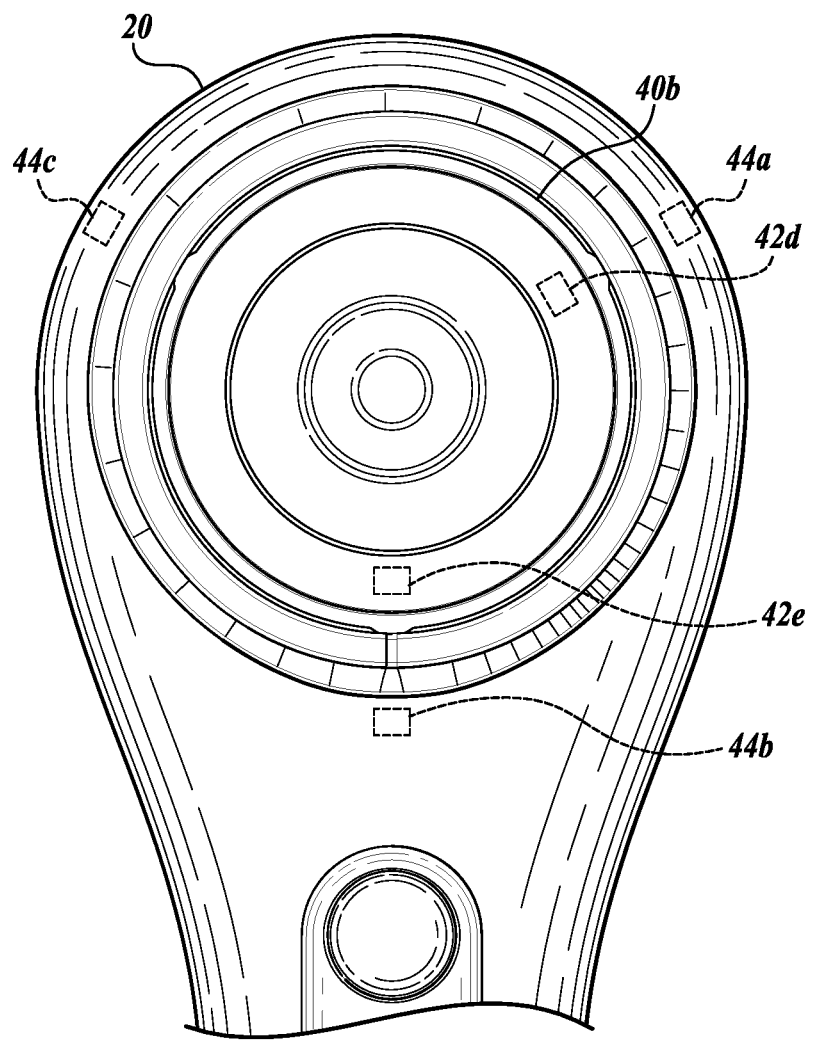
FIG. 3 is a side view of the system of FIG. 2 coupled to another end effector.

In an embodiment, the number of detectable elements associated with an end effector 40 is fewer than the number of sensors. In that regard, attention is directed to FIG. 3, where representative embodiments of a system 20 are illustrated that includes sensors 44a, 44b, and 44c. As shown, detectable elements 42d and 42e are associated with the end effector 40b. Sensors 44a and 44b are configured to detect an attribute associated with detectable elements 42d and 42e, respectively. As shown, the end effector 40b does not include a detectable element immediately proximate or corresponding to sensor 44c. In this regard, the system 20 is configured to distinguish between end effectors 40a and 40b at least in part on the basis of a different number of detectable elements associated with each end effector. Accordingly, as will be described further herein, the system 20 is configured to operate the motor 60 to execute different protocols associated with each end effector 40a and 40b.

Figure 4:
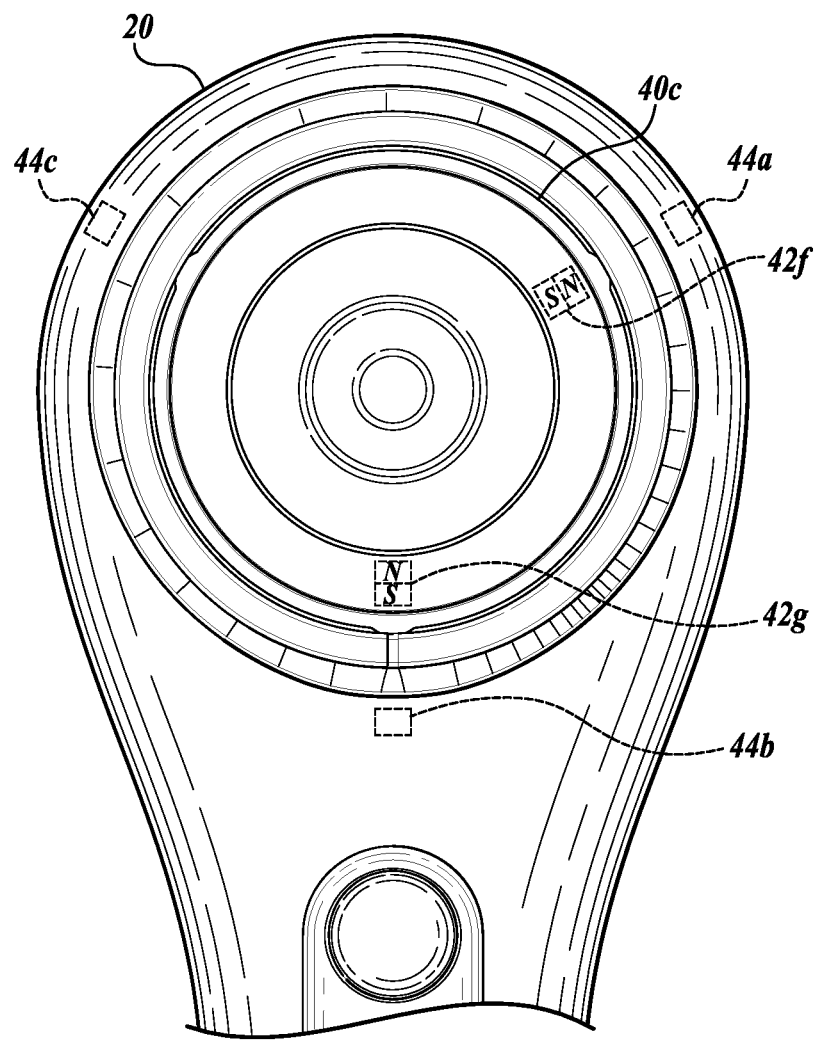
FIG. 4 is a side view of the system of FIG. 2 coupled to another end effector.

In an embodiment, the system 20 includes a sensor 44 is configured to detect an attribute associated with the detectable element 42 chosen from a location, a polarity, a magnetic susceptibility, a magnitude of a magnetic field, and a capacitance. For example, FIG. 4 illustrates a system 20 including end effector 40c carrying detectable elements 42f and 42g, wherein the detectable elements 42f and 42g are magnets carried at positions on end effector 40c. As shown, magnetic detectable elements 42f and 42g each have a polarity, represented by poles N and S. Further, as shown, detectable element 42f is carried by end effector 40c at a position and in an orientation with respect to sensor 44a so that pole N is closer to sensor 44a than pole S. Accordingly, in an embodiment, sensor 44a is configured to detect the presence or absence of detectable element 42f and also its orientation with respect to sensor 44a. Likewise, detectable element 42g is carried by end effector 40c at a position and in an orientation with respect to sensor 44b so that pole S is closer to sensor 44b than pole N. Accordingly, in an embodiment, sensor 44b is configured to detect the presence or absence of detectable element 42g and also its orientation with respect to sensor 44b.

In this regard, the system 20 is configured to detect a number of levels of encoding of an end effector 40 in addition to the presence or absence of one or more detectable elements 42. Such additional levels of encoding allow the system 20 to identify many different end effectors 40. For example, a system including three sensors configured to detect the presence or absence of up to three detectable elements and an attribute of that detectable element 42, such as a magnetic polarity, is configured to individually identify eleven different end effectors 40.

In an embodiment, the system 20 includes a computing arrangement including circuitry configured to actuate the motor 60 and to determine an inertia of the end effector 40. In that regard, attention is now turned to FIG. 5, where a schematic representation of a system 20, in accordance with the present aspect, is illustrated. In the embodiment shown, electronics interact with the end effector 40d, including detectable element 42e, to identify the end effector 40d. In the embodiment shown, the electronics include a computing arrangement 80, a motor 60, and a power storage source 100, such as a rechargeable battery. The computing arrangement 80, in some embodiments, includes circuitry 82, such as memory 84 and a microprocessor 86, that is configured and arranged to control the operation of the motor 60.

In an embodiment, the computing arrangement 80 includes circuitry 82 configured to actuate the motor 60 and to determine an inertia of the end effector 40d based on one or more signal parameters associated with actuation of the motor 60. In an embodiment, the one or more signal parameters associated with actuation of the motor 60 are chosen from a signal amplitude, a signal frequency, and a signal waveform shape. In an embodiment, the computing arrangement 80 including circuitry 82 configured to actuate the motor 60 and to determine an inertia of the end effector 40d is configured to determine a rotational inertia of the end effector 40d. In this regard and in accordance with certain embodiments, the computing arrangement 80 is configured to actuate the motor 60 with a known force to oscillate the end effector 40d about a starting position; count the number of times the end effector 40d passes the starting position in a given time; and calculate the rotational inertia of the end effector 40d. In an embodiment, the computing arrangement 80 is configured to determine a rotational inertia of the end effector 40d, wherein the computing arrangement 80 is configured to: actuate the motor 60 with a known force to oscillate the end effector 40d about a starting position; measure a maximum amplitude of the end effector 40d oscillation after a given time; and calculate the rotational inertia of the end effector 40d.

As above, in an embodiment, the computing arrangement 60 includes circuitry 82 configured to actuate the motor 60 and to determine the inertia of the end effector 40 based on one or more signal parameters associated with actuation of the motor 60. In an embodiment the signals are generated by one or more sensors 44a and 44b in response to a detectable element 42e.

In an embodiment, the system 20 includes two or more end effectors 40 configured to operably couple with the motor 60. In that regard, attention is now turned to FIG. 6 where a schematic representation of a system 20, in accordance with the present aspect, is illustrated. In the embodiment shown, the system 20 includes a first end effector 40e including a detectable element 42f. As shown, the first end effector 40e is operably coupled to the motor 60. The system 20 includes sensors 44a and 44b configured to detect the presence or absence of a detectable element associated with either detachable end effectors 40e or 40f operably coupleable to the motor 60. As shown, sensor 44a is configured to detect the presence of detectable element 42f, whereas sensor 44b is configured to detect the absence of a detectable element opposite detectable element 42f. Additionally, the system 20 includes a second end effector 40f including detectable elements 42g and 42h. In an embodiment, the motor 60 is configured to operably couple to the second end effector 40f when the first end effector 40e is not in use. Further, sensors 44a and 44b are configured to detect detectable elements 42g and 42h, respectively, when end effector 40f is operably coupled to the motor 60.

In an embodiment, the second end effector 40f has an inertia different from the first end effector 40e. In this regard, the system 20 is configured to differentiate between the first end effector 40e and the second end effector 40f based on a difference in inertia of the end effectors 40e and 40f and any differences in detectable elements 42f, 42g, and 42h associated with their respective end effectors, 40e and 40f.

In an embodiment, the computing arrangement 80 includes circuitry 82, such as a microprocessor 86 and memory 84, that is configured and arranged to control the operation of the motor 60. In some embodiments, the memory 84 includes one or more programs, which, for example, when executed by the microprocessor 86 causes the motor 60 to be operated according to a treatment regimen or protocol.

In an embodiment, the system 20 is configured with at least two drive modes that drive an end effector 40, such as a brush head, in a manner that effectuates at least two treatment regimens or protocols, such as protocol 1 and protocol 2. Accordingly, in certain embodiments, when an end effector is identified by the computing arrangement 80, the computing arrangement 80 is programmed to execute a protocol corresponding to the identified end effector 40 and actuate the motor 60. In this regard, the system 20 is configured to couple with one or more end effectors, 40e and 40f, and through detecting the presence or absence of detectable elements 42 and determining an inertia of the end effector 40, operate the motor 60 according to a protocol corresponding to the particular end effector 40e or 40f coupled to the motor 60.

Accordingly, in an embodiment, the computing arrangement 80 includes circuitry 82 configured to modulate one or more of an operating frequency, an operating duration, an operating intensity, a haptic protocol, a treatment protocol, and a duty cycle responsive to one or more inputs indicative of a detected element 42 and a determined inertia of an end effector 40. In an embodiment, the one or more inputs are indicative of a detectable element 42 are an attribute associated with the detectable element 42.

In another aspect, the present disclosure provides a system 20 includes an end effector 40 operably coupled to a motor 60, the end effector 40 including a number of detectable elements 42 greater than or equal to zero; a plurality of sensors 44 configured to detect the presence or absence of the number of detectable elements 42; and a computing arrangement 80 including circuitry 82 configured to actuate the motor 60 and to determine an inertia of the end effector 40; wherein the computing arrangement 80 is configured to identify the end effector 40 based on a measurand associated with the number detectable elements 42 and the inertia of the end effector 40.

In an embodiment, the measurand is chosen from a geometric configuration, a location, a polarity, a magnetic susceptibility, a magnitude of a magnetic field, and a capacitance of the number of detectable elements 42.

In another aspect, the present disclosure provides a method of identifying an end effector 40 coupled to a motor 60 of a system 20. A representative method of using the system 20 with a first end effector 40e and a second end effector 40f will now be described in some detail with respect to FIG. 6. As discussed further herein, by identifying an end effector 40 coupled to the motor 60 of the system 20, the system 20 can operate a motor 60 according to a treatment regimen or protocol corresponding to and appropriate for the particular end effector 40 coupled to the system 20.

In an embodiment, the method includes: detecting, with one or a plurality of sensors 44, the presence or absence of a number of detectable elements 42 associated with the end effector 40, the number of detectable elements 42 being greater than or equal to zero; actuating the motor 60 to determine an inertia of the end effector 40; and determining the identity of the end effector 40 based on the presence or absence of the number of detectable elements 42 and the inertia of the end effector 40.

In an embodiment, the method includes generating inertia information associated with the end effector 40; and determining the identity of the end effector 40 based on the presence or absence of a number of detectable elements 42 associated with the end effector 40 and at least one input indicative of the inertia of the end effector 40.

In an embodiment, determining an inertia of the end effector 40 includes generating inertia information associated with the end effector 40. In an embodiment, generating inertia information associated with the end effector 40 includes generating rotational inertia information associated with the end effector 40. In an embodiment, rotational inertia information is generated by: actuating the motor 60 with a known force to oscillate the end effector 40 about a starting position; counting the number of times the end effector 40 passes the starting position in a given time; and calculating the rotational inertia of the end effector 40. In an embodiment, a motor spring constant is fixed. By altering a rotational inertia of an attached end effector 40 the system 20 determines a natural frequency of the system 20 and calculates the inertia of the attached end effector 40.

In an embodiment, generating inertia information associated with the end effector 40 includes actuating the motor 60 and monitoring a change in a change in load to determine inertia information associated with of the end effector 40.

In an embodiment, rotational inertia information is generated by: actuating the motor 60 with a known force to oscillate the end effector 40 about a starting position; measuring a maximum amplitude of the end effector 40 oscillation decay after a given time; and calculating the rotational inertia of the end effector 40. In an embodiment, a damping coefficient of the system 20 is held constant and the method includes measuring when end effector 40 oscillation reaches a particular amplitude.

As above, the method of identifying an end effector 40 coupled to a motor 60 of a system 20 includes detecting, with a plurality of sensors 44, the presence or absence of a number of detectable elements 42 associated with the end effector 40, the number of detectable elements 42 being greater than or equal to zero. As described further herein, by identifying the end effector 40, the system is configured to execute a protocol corresponding to the identified end effector.

In an embodiment, detecting the presence or absence of a number of detectable elements 42 includes detecting an attribute associated with the number of detectable elements 42. In an embodiment, the attribute associated with the number of detectable elements 42 includes an attribute chosen from a location, a polarity, a magnetic susceptibility, a magnitude of a magnetic field, and a capacitance of the number of detectable elements 42.

In an embodiment, the number of detectable elements 42 includes two or more detectable elements 42. In such embodiments, detecting the presence or absence of a number of detectable elements 42 includes detecting an attribute associated with the number of detectable elements 42, wherein the attribute is chosen from a geometric configuration, a location, a polarity, a magnetic susceptibility, a magnitude of a magnetic field, and a capacitance of the two or more detectable elements.

Certain embodiments disclosed herein utilize circuitry in order to implement treatment protocols, operably couple two or more components, generate information, determine operation conditions, control an appliance or method, and/or the like. Circuitry of any type can be used. In an embodiment, circuitry includes, among other things, one or more computing devices such as a processor (e.g., a microprocessor), a central processing unit (CPU), a digital signal processor (DSP), an application-specific integrated circuit (ASIC), a field-programmable gate array (FPGA), or the like, or any combinations thereof, and can include discrete digital or analog circuit elements or electronics, or combinations thereof. In an embodiment, circuitry includes one or more ASICs having a plurality of predefined logic components. In an embodiment, circuitry includes one or more FPGA having a plurality of programmable logic components.

In an embodiment, circuitry includes hardware circuit implementations (e.g., implementations in analog circuitry, implementations in digital circuitry, and the like, and combinations thereof). In an embodiment, circuitry includes combinations of circuits and computer program products having software or firmware instructions stored on one or more computer readable memories that work together to cause a device to perform one or more methodologies or technologies described herein. In an embodiment, circuitry includes circuits, such as, for example, microprocessors or portions of microprocessor, that require software, firmware, and the like for operation. In an embodiment, circuitry includes an implementation comprising one or more processors or portions thereof and accompanying software, firmware, hardware, and the like. In an embodiment, circuitry includes a baseband integrated circuit or applications processor integrated circuit or a similar integrated circuit in a server, a cellular network device, other network device, or other computing device. In an embodiment, circuitry includes one or more remotely located components. In an embodiment, remotely located components are operably coupled via wireless communication. In an embodiment, remotely located components are operably coupled via one or more receivers, transmitters, transceivers, or the like.

In an embodiment, circuitry includes one or more memory devices that, for example, store instructions or data. Non-limiting examples of one or more memory devices include volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like), persistent memory, or the like. Further non-limiting examples of one or more memory devices include Erasable Programmable Read-Only Memory (EPROM), flash memory, or the like. The one or more memory devices can be coupled to, for example, one or more computing devices by one or more instructions, data, or power buses.

In an embodiment, circuitry of the system 20 includes one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In an embodiment, circuitry includes one or more user input/output components that are operably coupled to at least one computing device to control (electrical, electro-mechanical, software-implemented, firmware-implemented, or other control, or combinations thereof) at least one parameter associated with the application of cyclical movement by the system 20, for example, controlling the duration and peak cyclic or oscillation frequency of the end effector of the system 20.

In an embodiment, circuitry of the system 20 includes a computer-readable media drive or memory slot configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as any form of flash memory, magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. The term "about" means plus or minus 5% of the stated value.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

While illustrative embodiments have been illustrated and described, it will be appreciated that various changes can be made therein without departing from the spirit and scope of the invention.

The embodiments of the invention in which an exclusive property or privilege is claimed are defined as follows:

1. A system, comprising:
    a first sensor configured to detect a presence or absence of a detectable element associated with a detachable end effector operably coupled to a motor; and
    a computing arrangement including circuitry configured to actuate the motor with a known force and to determine an inertia of the end effector.

2. The system of claim 1, wherein the first sensor is configured to detect an attribute associated with the detectable element chosen from a location, a polarity, a magnetic susceptibility, a magnitude of a magnetic field, and a capacitance.

3. The system of claim 1, wherein the first sensor is configured to detect an attribute associated with two or more detectable elements chosen from a geometric configuration, a location, a polarity, a magnetic susceptibility, a magnitude of a magnetic field, and a capacitance.

4. The system of claim 1, wherein the computing arrangement includes circuitry configured to actuate the motor and to determine the inertia of the end effector based on one or more signal parameters associated with actuation of the motor chosen from a signal amplitude, a signal frequency, and a signal waveform shape.

5. The system of claim 4, wherein the computing arrangement including circuitry configured to actuate the motor and to determine an inertia of the end effector is configured to determine a rotational inertia of the end effector, and wherein the computing arrangement is configured to:
    actuate the motor with the known force to oscillate the end effector about a starting position;
    count the number of times the end effector passes the starting position in a given time; and
    calculate the rotational inertia of the end effector.

6. The system of claim 4, the computing arrangement including circuitry to actuate the motor and to determine an inertia of the end effector is configured to determine a rotational inertia of the end effector, and wherein the computing arrangement is configured to:
    actuate the motor with the known force to oscillate the end effector about a starting position;
    measure a maximum amplitude of the end effector oscillation after a given time; and
    calculate the rotational inertia of the end effector.

7. The system of claim 1, wherein the computing arrangement includes circuitry configured to modulate one or more of an operating frequency, an operating duration, an operating intensity, a haptic protocol, a treatment protocol, and a duty cycle responsive to one or more inputs indicative of a detected element and a determined inertia of the end effector.

8. The system of claim 7, wherein the one or more inputs indicative of a detected element are an attribute associated with the detectable element.

9. The system of claim 1, wherein the detectable element includes at least one magnet,
    and wherein the first sensor is chosen from a Hall effect sensor, a capacitance sensor, an inductance sensor, and a magnetic susceptibility.

10. The system of claim 1, further comprising a second sensor associated with the system, wherein the second sensor is configured to detect a presence or absence of a detectable element associated with the end effector.

11. The system of claim 10, wherein the second sensor is configured to detect an attribute associated with the detectable element chosen from a location, a polarity, a magnetic susceptibility, a magnitude of the magnetic field, and a capacitance.

12. The system of claim 10, wherein the number of sensors is greater than the number of detectable elements.

13. The system of claim 1, wherein the computing arrangement is configured to identify the end effector based on the presence or absence of the detectable element and the inertia of the end effector.

14. The system of claim 1, wherein the end effector is a first end effector, wherein the motor is configured to operably couple to a second end effector when the first end effector is not in use, and wherein the computing arrangement includes circuitry configured to modulate one or more of an operating frequency, an operating duration, an operating intensity, a haptic protocol, a treatment protocol, and a duty cycle responsive to one or more inputs indicative of a detected element and a determined inertia of the second end effector.

15. The system of claim 14, wherein the second end effector includes a second detectable element different from the detectable element of the first end effector; and wherein the first sensor is configured to detect signals indicative of the presence or absence of the second detectable element.

16. The system of claim 14, wherein the second end effector has an inertia different from the first end effector.

17. An appliance, comprising:
    an end effector operably coupled to a motor, the end effector including a number of detectable elements greater than or equal to zero;
    a plurality of sensors configured to detect the presence or absence of the number of detectable elements; and
    a computing arrangement including circuitry configured to actuate the motor with a known force and to determine an inertia of the end effector; wherein the computing arrangement is configured to identify the end effector based on a measurand associated with the number detectable elements and the inertia of the end effector.

18. A method of identifying an end effector coupled to a motor of a system comprising:
    actuating the motor with a known force;
    generating inertia information associated with the end effector; and
    determining the identity of the end effector based on the presence or absence of a number of detectable elements associated with the end effector and at least one input indicative of the inertia of the end effector.

19. The method of claim 18, wherein generating inertia information associated with the end effector includes generating rotational inertia information; and wherein the rotational inertia information is generated by:
  actuating the motor with the known force to oscillate the end effector about a starting position;
  counting the number of times the end effector passes the starting position in a given time; and
  calculating the rotational inertia of the end effector.

20. The method of claim 18, wherein generating inertia information associated with the end effector includes generating rotational inertia information; and wherein the rotational inertia information is generated by:
  actuating the motor with the known force to oscillate the end effector about a starting position;
  measuring a maximum amplitude of the end effector oscillation decay after a given time; and
  calculating the rotational inertia of the end effector.

\* \* \* \* \*

UNITED STATES PATENT AND TRADEMARK OFFICE
CERTIFICATE OF CORRECTION

PATENT NO. : 10,603,799 B2
APPLICATION NO. : 15/639544
DATED : March 31, 2020
INVENTOR(S) : S. Straka Page 1 of 1

It is certified that error appears in the above-identified patent and that said Letters Patent is hereby corrected as shown below:

In the Claims

| Column | Line | |
|--------|------|---|
| 11 | 55 | In Claim 6, Please change "the" to -- wherein the --. |
| 12 | 56 | In Claim 17, Please change "number" to -- number of --. |

Signed and Sealed this
Twenty-seventh Day of October, 2020

Andrei Iancu
*Director of the United States Patent and Trademark Office*